(12) United States Patent
Paulk et al.

(10) Patent No.: US 10,449,032 B2
(45) Date of Patent: Oct. 22, 2019

(54) LOCKING SUTURE ANCHOR DELIVERY DEVICE

(71) Applicant: Smith & Nephew, Inc., Memphis, TN (US)

(72) Inventors: David A. Paulk, Hopedale, MA (US); Richard M. Lunn, Kingston, MA (US)

(73) Assignee: Smith & Nephew, Inc., Memphis, TN (US)

( * ) Notice: Subject to any disclaimer, the term of this patent is extended or adjusted under 35 U.S.C. 154(b) by 647 days.

(21) Appl. No.: 15/071,783

(22) Filed: Mar. 16, 2016

(65) Prior Publication Data
US 2016/0193034 A1    Jul. 7, 2016

Related U.S. Application Data

(62) Division of application No. 13/509,167, filed as application No. PCT/US2010/056160 on Nov. 10, 2010, now Pat. No. 9,314,240.

(60) Provisional application No. 61/259,732, filed on Nov. 10, 2009.

(51) Int. Cl.
 *A61B 17/04*   (2006.01)
 *A61F 2/08*    (2006.01)
 *A61B 17/86*   (2006.01)

(52) U.S. Cl.
 CPC ........ *A61F 2/0811* (2013.01); *A61B 17/0401* (2013.01); *A61B 17/864* (2013.01); *A61B 2017/044* (2013.01); *A61B 2017/0409* (2013.01); *A61B 2017/0414* (2013.01); *A61B 2017/0427* (2013.01); *A61B 2017/0437* (2013.01); *A61B 2017/0441* (2013.01); *A61B 2017/0445* (2013.01); *A61B 2017/0453* (2013.01); *A61B 2017/0464* (2013.01); *A61F 2002/0823* (2013.01); *A61F 2002/0858* (2013.01); *A61F 2002/0888* (2013.01)

(58) Field of Classification Search
 USPC ............ 606/60, 64, 104, 139, 151, 232, 246
 See application file for complete search history.

(56) References Cited

U.S. PATENT DOCUMENTS

| 4,738,255 A | 4/1988  | Goble et al. |
| 4,901,721 A | 2/1990  | Hakki |
| 5,152,790 A | 10/1992 | Rosenberg et al. |
| 5,464,427 A | 11/1995 | Curtis et al. |

(Continued)

FOREIGN PATENT DOCUMENTS

| EP | 0673624    | 9/1995 |
| EP | 0673624 A2 | 9/1995 |

(Continued)

OTHER PUBLICATIONS

Second Office Action for Chinese Application No. 201080050979.3, dated Nov. 14, 2014.

(Continued)

*Primary Examiner* — Vy Q Bui
(74) *Attorney, Agent, or Firm* — Burns & Levinson, LLP; Joseph M. Maraia (57) ABSTRACT

A suture anchor delivery device includes a handle and first and second knobs coupled to the handle. A shaft is coupled to the handle and the shaft includes an outer member, an inner member disposed within the outer member and a driver disposed within the inner member.

19 Claims, 7 Drawing Sheets

(56) References Cited

U.S. PATENT DOCUMENTS

| | | | |
|---|---|---|---|
| 5,671,505 | A | 9/1997 | Anscher |
| 5,827,291 | A | 10/1998 | Fucci et al. |
| 5,948,000 | A | 9/1999 | Larsen et al. |
| 6,648,903 | B1 | 11/2003 | Pierson, III |
| 7,329,272 | B2 | 2/2008 | Burkhart et al. |
| 7,390,329 | B2 | 6/2008 | Westra et al. |
| 7,678,134 | B2 | 3/2010 | Schmieding et al. |
| 8,454,654 | B2 | 6/2013 | Ferragamo et al. |
| 8,764,798 | B2 | 7/2014 | Housman |
| 8,858,565 | B1 * | 10/2014 | Hoof .................. A61B 17/8888 606/104 |
| 9,179,907 | B2 | 11/2015 | ElAttrache et al. |
| 2002/0013608 | A1 | 1/2002 | ElAttrache et al. |
| 2002/0052630 | A1 | 5/2002 | Morgan et al. |
| 2004/0138683 | A1 | 7/2004 | Shelton et al. |
| 2004/0138706 | A1 | 7/2004 | Abrams et al. |
| 2004/0225292 | A1 | 11/2004 | Sasso et al. |
| 2005/0033363 | A1 | 2/2005 | Bojarski et al. |
| 2005/0055052 | A1 | 3/2005 | Lombardo et al. |
| 2005/0090827 | A1 | 4/2005 | Gedebou |
| 2005/0245932 | A1 | 11/2005 | Fanton et al. |
| 2005/0256530 | A1 | 11/2005 | Petros |
| 2006/0106423 | A1 | 5/2006 | Weisel et al. |
| 2006/0246396 | A1 | 11/2006 | Suttin et al. |
| 2006/0271060 | A1 | 11/2006 | Gordon |
| 2007/0112385 | A1 | 5/2007 | Conlon |
| 2008/0009904 | A1 | 1/2008 | Bourque et al. |
| 2008/0033487 | A1 | 2/2008 | Schwartz et al. |
| 2008/0103528 | A1 | 5/2008 | Zirps et al. |
| 2009/0054928 | A1 | 2/2009 | Denham |
| 2009/0082805 | A1 | 3/2009 | Kaiser et al. |
| 2009/0112270 | A1 | 4/2009 | Lunn et al. |
| 2009/0157124 | A1 | 6/2009 | Ferragamo et al. |
| 2009/0312763 | A1 * | 12/2009 | McCormack ........ A61B 17/025 606/83 |
| 2009/0312776 | A1 | 12/2009 | Kaiser et al. |
| 2010/0063542 | A1 | 3/2010 | van der Burg et al. |
| 2010/0114162 | A1 | 5/2010 | Bojarski |
| 2010/0160963 | A1 | 6/2010 | Fallin et al. |
| 2010/0256678 | A1 | 10/2010 | Ducharme |
| 2010/0318125 | A1 | 12/2010 | Gerber et al. |
| 2011/0004242 | A1 | 1/2011 | Stchur |
| 2011/0004243 | A1 | 1/2011 | Dreyfuss |
| 2011/0112576 | A1 | 5/2011 | Nguyen et al. |
| 2013/0006302 | A1 | 1/2013 | Paulk |
| 2013/0085529 | A1 | 4/2013 | Housman |

FOREIGN PATENT DOCUMENTS

| | | | |
|---|---|---|---|
| JP | 2000-512193 | A | 9/2000 |
| JP | 2005504555 | | 2/2005 |
| JP | 2005504555 | A | 2/2005 |
| JP | 2007271773 | | 10/2007 |
| JP | 2000512193 | | 9/2009 |
| JP | 2011-517605 | A | 6/2011 |
| WO | 9529637 | | 11/1995 |
| WO | 9842261 | A1 | 10/1998 |
| WO | 199842261 | | 10/1998 |
| WO | 0243576 | A2 | 6/2002 |
| WO | 200243576 | | 6/2002 |
| WO | 2004037094 | | 5/2004 |
| WO | 2009055800 | | 4/2009 |
| WO | 2009055800 | A1 | 4/2009 |

OTHER PUBLICATIONS

Patent Examination Report No. 1 for Australian Application No. 2010319662, dated Feb. 11, 2015.
Office Action for Russian Application No. 2012122881/14(0347786), dated Dec. 1, 2014.
Notice of Reasons for Rejection for Japanese Application No. 2012-538929, dated Jul. 22, 2014.
First Office Action for Chinese Application No. 201080050979.3, dated Jun. 5, 2014.
Third Office Action for Chinese Application No. 201080050979.3, dated Apr. 24, 2015.
Patent Examination Report No. 2 for related Australian Patent Application No. 2010319662, dated Sep. 18, 2015.
Decision of Rejection for Japanese Application No. 2012-538929, dated Apr. 6, 2015.
Office Action for Russian Application No. 2012122881/14(034786), dated Mar. 18, 2015.
Patent Examination Report from related Australian Application No. 2012321349, dated Jun. 3, 2016.
Second Office Action from related Chinese Application No. 201280059495.4, dated May 26, 2016.
Office Action from related Japanese Application No. 2014-534541, dated Sep. 5, 2016.
Third Office Action from related Chinese Application No. 201280059495.4, dated Aug. 24, 2016.
Office Action from related Russian Application No. 2014114628/14(022908), dated Sep. 6, 2016.
Office Action from related Russian Application No. 201414628/14(022908), dated Dec. 22, 2016.
Office Action from related Chinese Application No. 201280059495.4, dated Dec. 29, 2016.
India's Application No. 4000/DELNP/2012 First Examination Report.
European Examination Report—Application No. 10781768.6-1113 dated Jul. 17, 2019.

* cited by examiner

LOCKING SUTURE ANCHOR DELIVERY DEVICE

CROSS-REFERENCE TO RELATED APPLICATIONS

This application is a divisional application of U.S. patent application Ser. No. 13/509,167 filed Sep. 6, 2012 which is a national stage application of PCT/US2010/056160, filed Nov. 10, 2010 which claims priority to U.S. provisional patent application No. 61/259,732 filed on Nov. 10, 2009.

BACKGROUND OF THE INVENTION

1. Field of the Invention

The present disclosure relates to tissue repair, and more specifically, to an anchor for securing tissue to bone.

2. Related Art

Arthroscopic procedures often require soft tissue to be reattached to bone. To achieve this, anchors are placed in the bone and sutures attached to the anchor are passed through the tissue to securely retain the tissue in place. When making a repair of soft tissue to bone, it is advantageous to have as large an area of contact between the bone and tissue as possible. Anchor points spaced from one another in rows result in a repair having a broader area of contact. A procedure, and components for use in such procedure, that securely attaches tissue to bone using a plurality of attachment points over a large area of contact is needed. Such procedure must be able to be done in a quick and efficient manner with a minimum of recovery time for the patient.

BRIEF SUMMARY OF THE INVENTION

In one embodiment, the present disclosure relates to an anchor delivery device for tissue repair including a handle; a first knob coupled to the handle; a second knob coupled to the handle; and a shaft coupled to the handle, the shaft including an outer member, an inner member disposed within the outer member and a driver disposed within the inner member. In another embodiment, a proximal portion of the driver is coupled to the first knob and a proximal portion of the outer member is coupled to the second knob. In another embodiment, the anchor delivery device further includes a sleeve coupled to the outer member, an anchor coupled to the inner member and an insertion member disposed within a cavity of the anchor, the insertion member coupled to the driver.

In another embodiment, a suture anchor delivery device includes a handle defining a cavity; and a shaft, coupled to the handle. The shaft includes a shaft outer member; a shaft inner member disposed within the shaft outer member. A first knob is coupled to the handle and a movable member is coupled to the first knob and a proximal portion of the shaft outer member. A second knob is coupled to the handle; and a driver, disposed within the shaft inner member, is coupled to the second knob.

In yet another embodiment, a suture anchor delivery device comprises a handle and a shaft coupled to the handle. A driver is disposed within the shaft and a movable member is disposed in the handle. A first knob is rotatably coupled to the movable member and configured to advance the movable member distally within the handle and a second knob is rotatably coupled to the driver and configured to advance the driver distally within the shaft.

Further features, aspects and advantages of the present disclosure, as well as the structure and operation of various embodiments of the present disclosure, are described in detail below with reference to the accompanying drawings.

BRIEF DESCRIPTION OF THE DRAWINGS

The accompanying drawings, which are incorporated in and form a part of the specification, illustrate the embodiments of the present invention and together with the description, serve to explain the principles of the invention. In the drawings.

DETAILED DESCRIPTION

This application claims priority of U.S. patent application Ser. No. 13/509,167, filed Sep. 6, 2012 which is a national stage application of PCT/US2010/056160, filed Nov. 10, 2010 which claims priority to U.S. provisional patent application No. 61/259,732 filed on Nov. 10, 2009, the disclosures of which are incorporated herein by reference in their entireties for all purposes.

The embodiments were chosen and described in order to best explain the principles of the invention and its practical application to thereby enable others skilled in the art to best utilize the invention in various embodiments and with various modifications as are suited to the particular use contemplated.

FIGS. 1-6 show the components of an anchor assembly 10 of the present disclosure. The assembly 10 includes an anchor 11, an insertion member 12 and a sleeve 13. The anchor 11 includes a distal portion 11a, a proximal portion 11b, a cavity 11c defined within the anchor 11 and an opening 11c' to the cavity 11c, a through hole 11d having two openings 11d', protrusions 11e located below each opening 11d and barbs 11f located on an outer surface 11a' of the distal portion 11a. The insertion member 12 includes a proximal portion 12a having threads 12a', a non-threaded distal portion 12b and a cannulation 12c. The sleeve 13 includes a threaded proximal portion 13a, a non-threaded distal portion 13b, a cavity 13c and an opening 13d to the cavity. The anchor cavity 11c includes threads 11c' that engage threads 12a' of the insertion member 12 upon insertion of the member 12 into the cavity 11c FIGS. 7-11 show the delivery device 20 for use with the anchor assembly of FIG. 1. The device 20 includes a handle 21, a first knob 22 coupled to the handle 21, a second knob 23 coupled to the handle 21 and a shaft 24 coupled to the handle 21. The shaft 24 includes an outer member 24a, an inner member 24b disposed within the outer member 24a and a driver 25 disposed within the inner member 24b.

As shown in FIGS. 8-11, a proximal portion 25a of the driver 25 is coupled to the second knob 23 and a proximal portion 26a of the outer member 24a is coupled to the first knob 22 via a movable member 27. The movable member 27 includes a distal portion 27a, a proximal portion 27b and a cannulation 27c. The movable member proximal portion 27b includes threads 27b' on its outer surface 27b". The movable member 27 is located in a cavity 21a of the handle 21. The handle cavity 21a includes a distal portion 21a' and a proximal portion 21a". The handle cavity proximal portion 21a" includes threads 21b that engage the movable member proximal portion outer surface threads 27b'. As will be explained further below, due to the threaded engagement of the movable member 27 with the cavity proximal portion 21a", rotation of the first knob 22 causes the outer member 24a to move axially along the length of the shaft 24. Rotation of the first knob 22 is discontinued when an end 27a' of the movable member distal portion 27a engages an end 21c of the cavity distal portion 21a', thereby preventing over-insertion of the sleeve 13 into the bone.

A proximal portion 25a of the driver 25 includes threads 25a' that engage threads 29 on an inner surface 24b' of the inner member 24b. Threaded engagement of the driver 25 and inner member 24b allow for axial movement of the driver 25 along the shaft 24 via rotation of the second knob 23. Rotation of the second knob 23 is discontinued when a depth stop 25b engages an end 24b" of the inner member 24b, thereby preventing over-insertion of the insertion member 12 into the anchor 11, as will be further explained below.

During tissue repair, suture is attached to a soft tissue, a hole is created in bone, ends of the suture are placed through the through hole 11d of the anchor 11, the anchor 11 is placed within the bone hole via axial advancement of the delivery device 20, the second knob 23 is rotated to move the insertion member 12 axially and engage and fixate the suture to the anchor 11. The first knob 22 is then rotated to move the sleeve 13 axially and place the distal end 13b of the sleeve 13 over the proximal end 11b of the anchor 11 and further lock the suture between the sleeve 13 and the bone.

Figure 1:
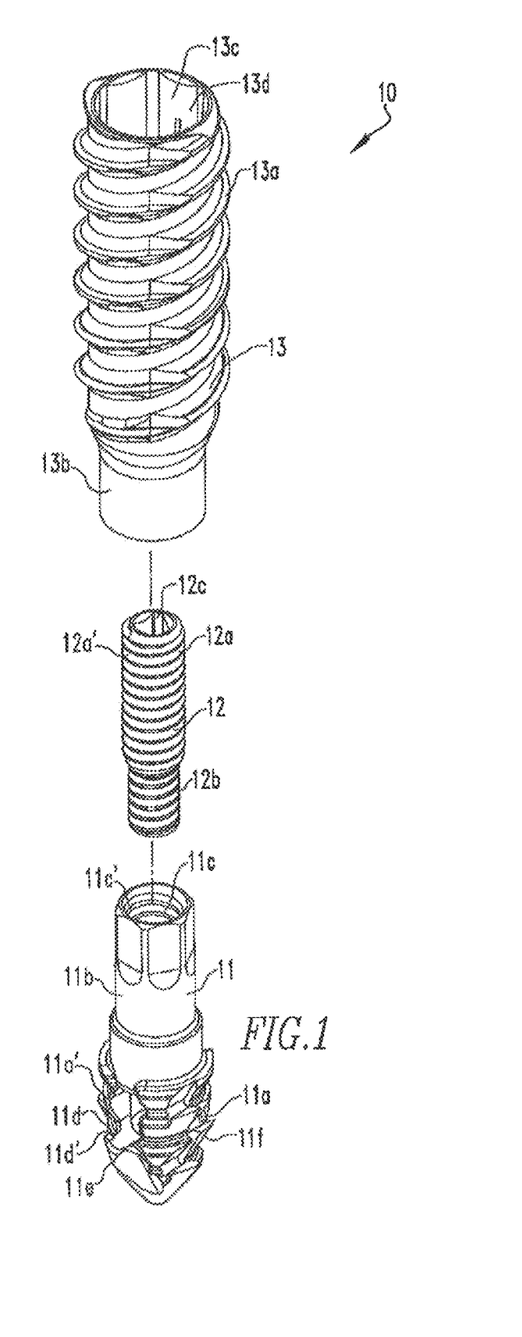
FIG. 1 shows an exploded view of the anchor assembly of the present disclosure.
Figure 2:
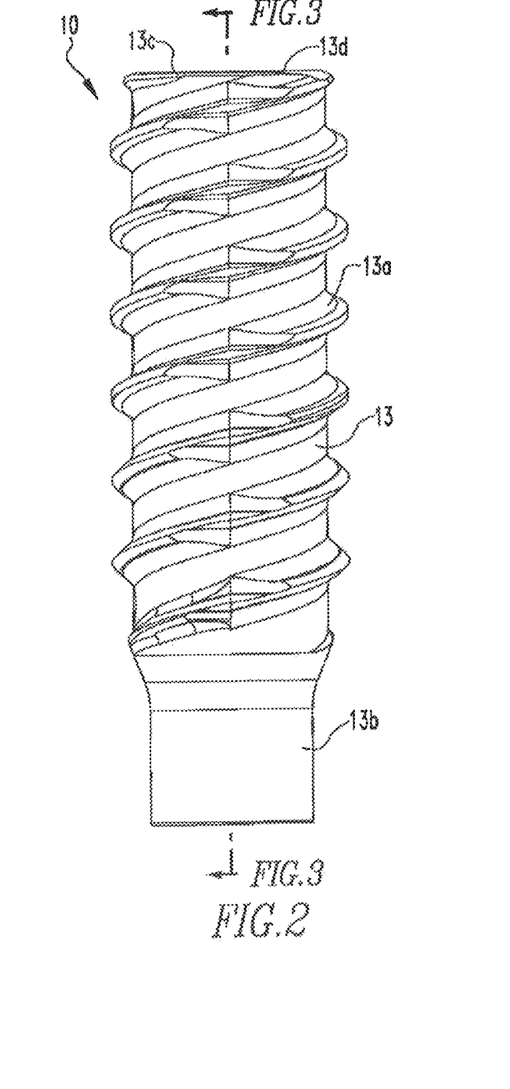
FIG. 2 shows a side view of the sleeve of the anchor assembly of FIG. 1.
Figure 3:
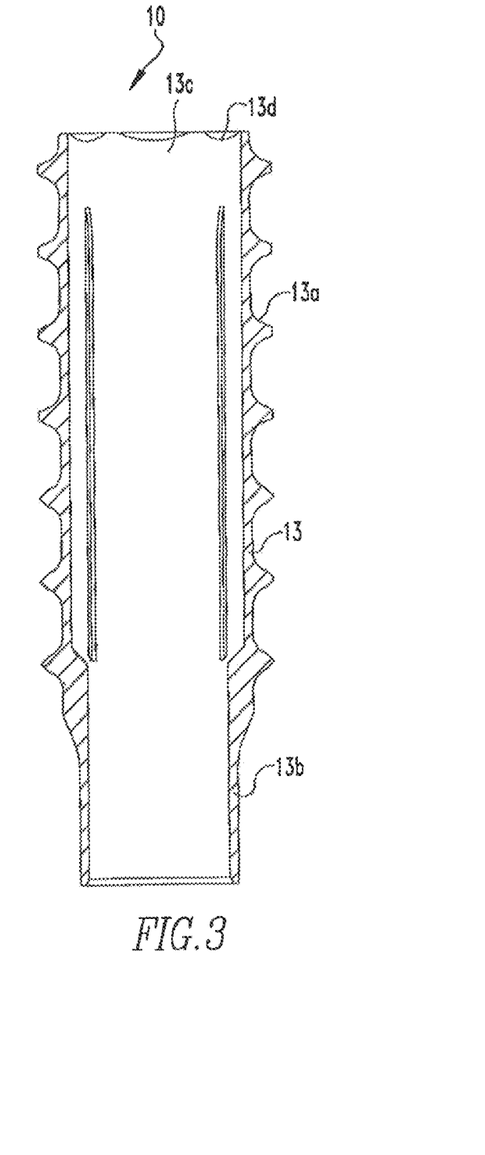
FIG. 3 shows a cross-sectional view of the sleeve of FIG. 2.
Figure 4:
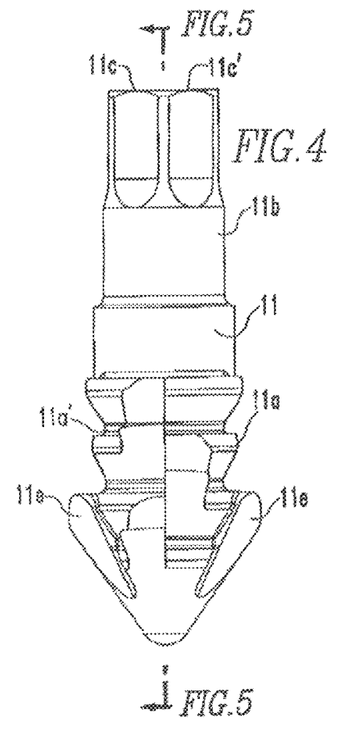
FIG. 4 shows a side view of the anchor of the anchor assembly of FIG. 1.
Figure 5:
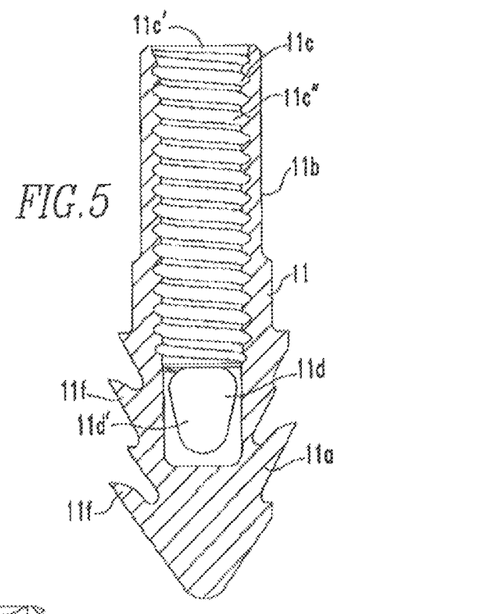
FIG. 5 shows a cross-sectional view of the anchor of the anchor of FIG. 4.
Figure 6:
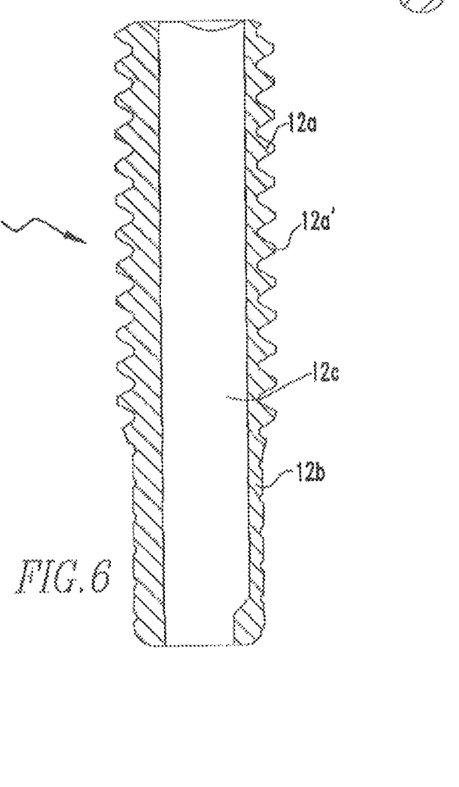
FIG. 6 shows a cross-sectional view of the insertion member of the anchor assembly of FIG. 1.
Figure 7:
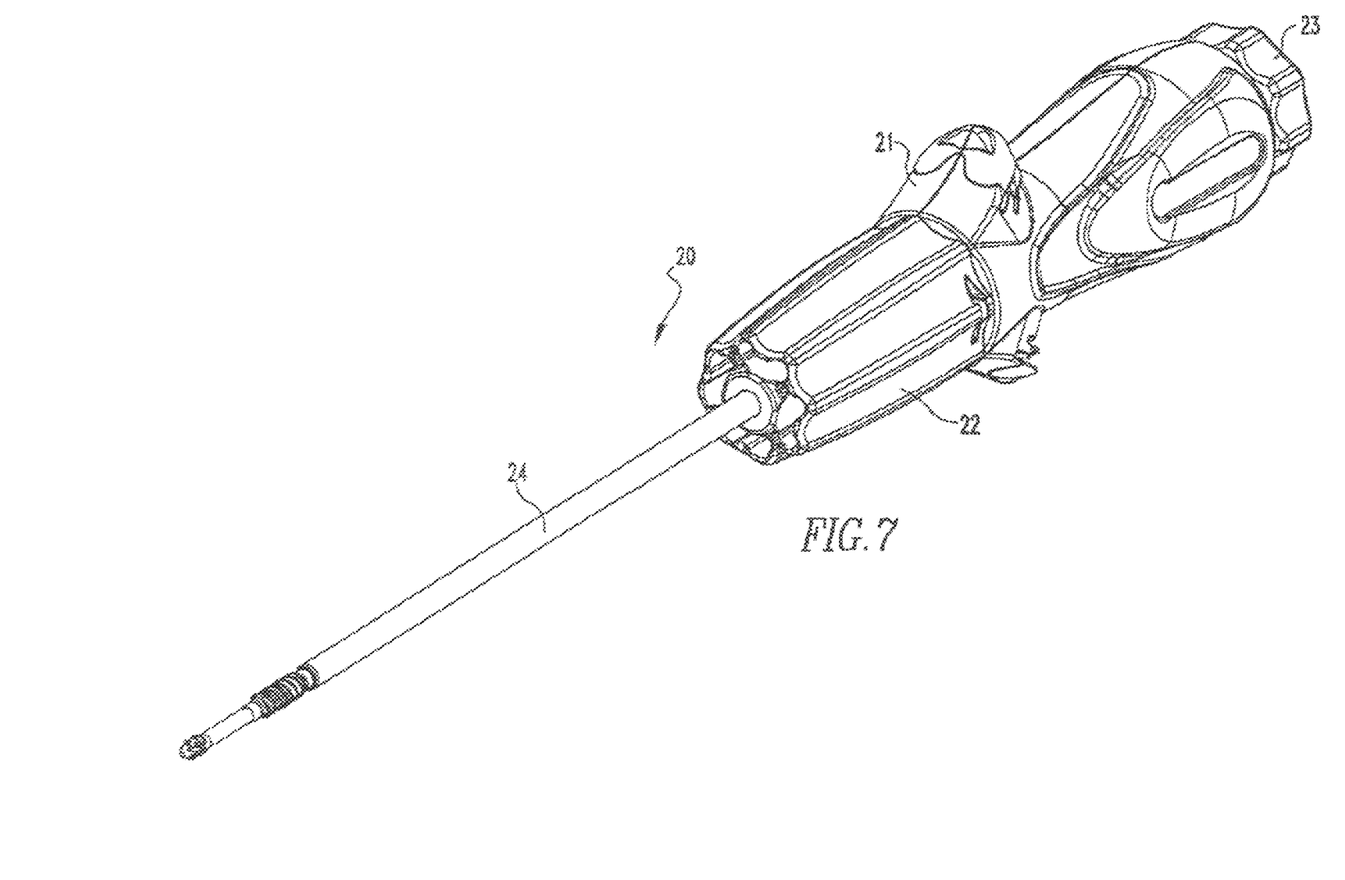
FIG. 7 shows an isometric view of the anchor delivery device of the present disclosure.
Figure 8:
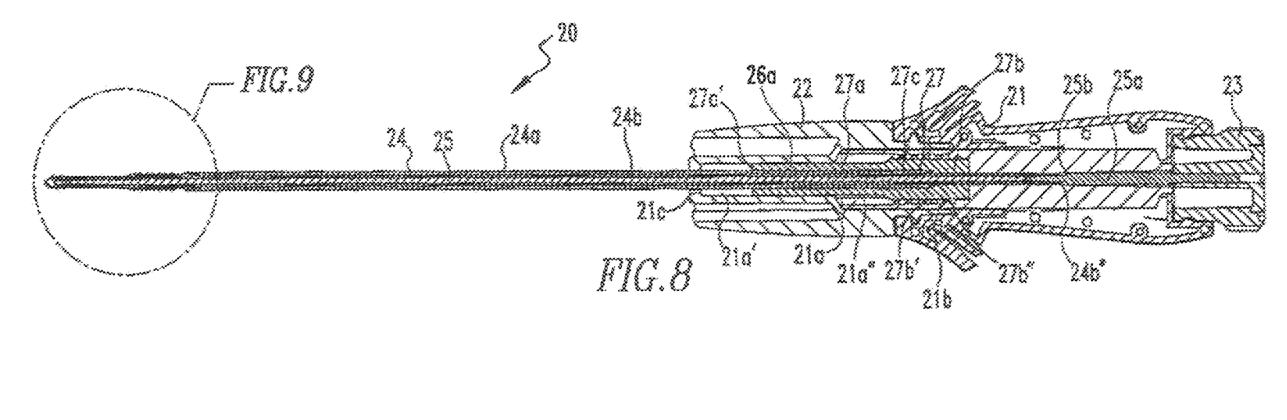
FIG. 8 shows a cross-sectional view of the anchor delivery device of FIG. 7 prior to insertion of the anchor assembly into bone.
Figure 9:
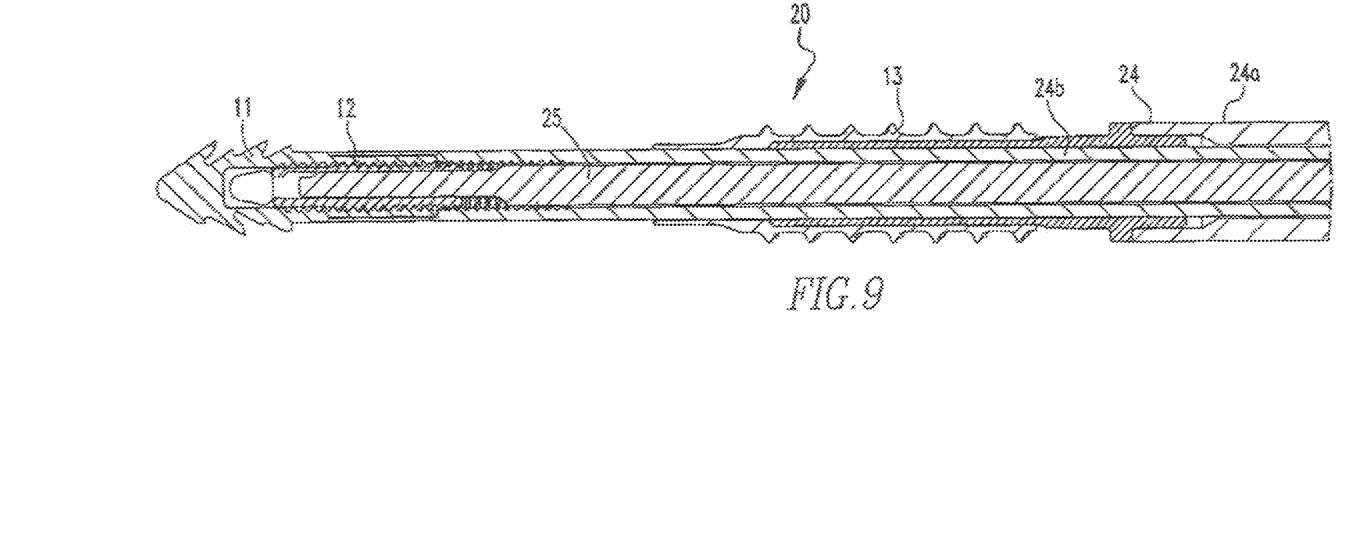
FIG. 9 shows an expanded view of the distal end of the shaft of the anchor delivery device of FIG. 8.
Figure 10:
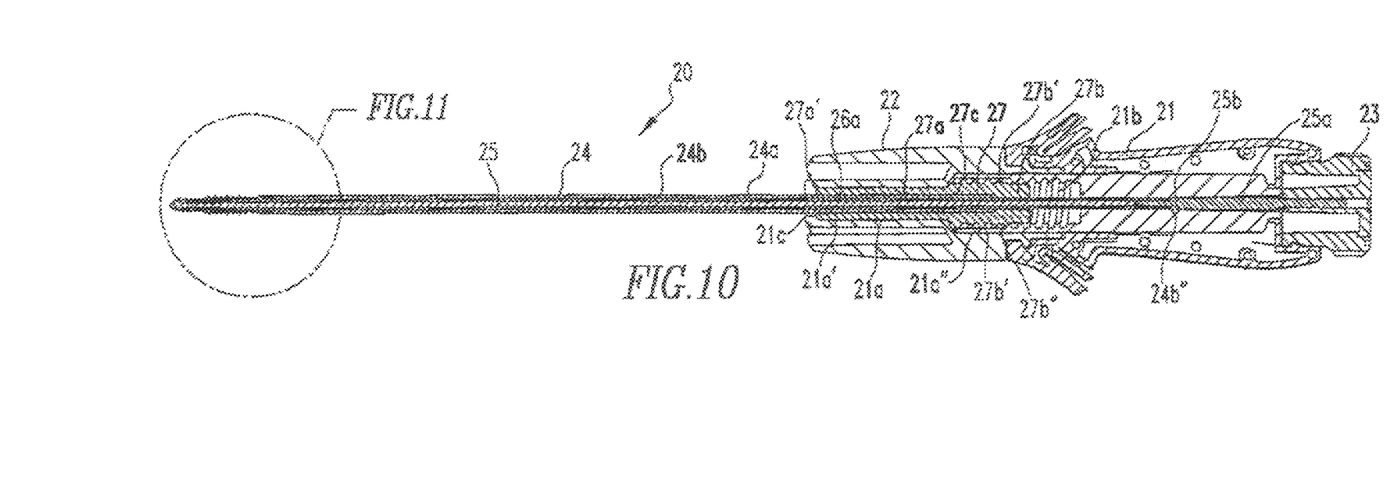
FIG. 10 shows a cross-sectional view of the anchor delivery device of FIG. 7 after insertion of the anchor assembly into bone.
Figure 11:
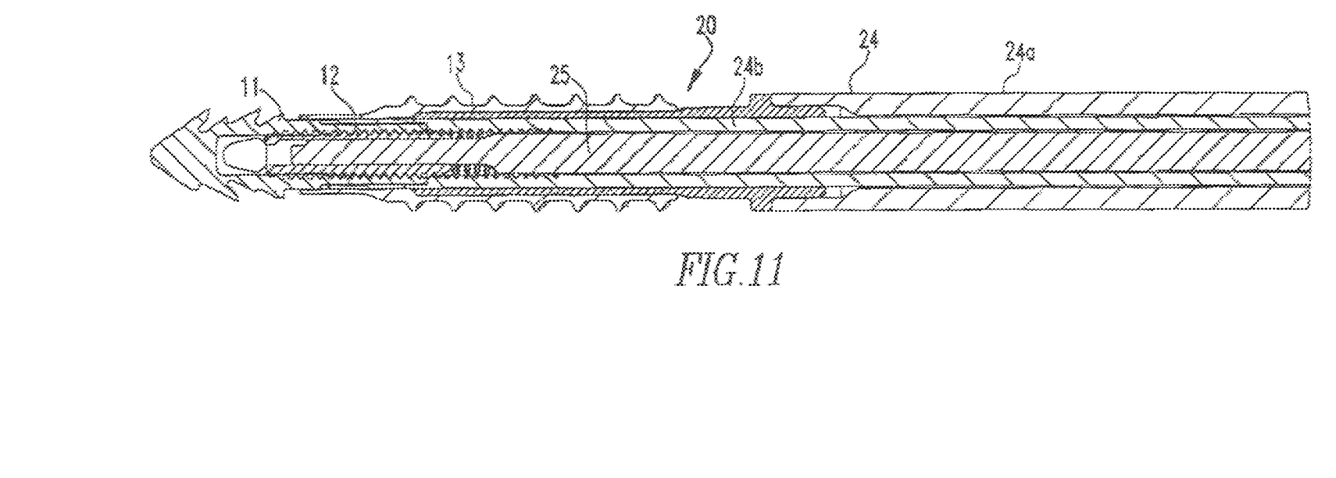
FIG. 11 shows an expanded view of the distal end of the shaft of the anchor delivery device of FIG. 10.
Figure 12:
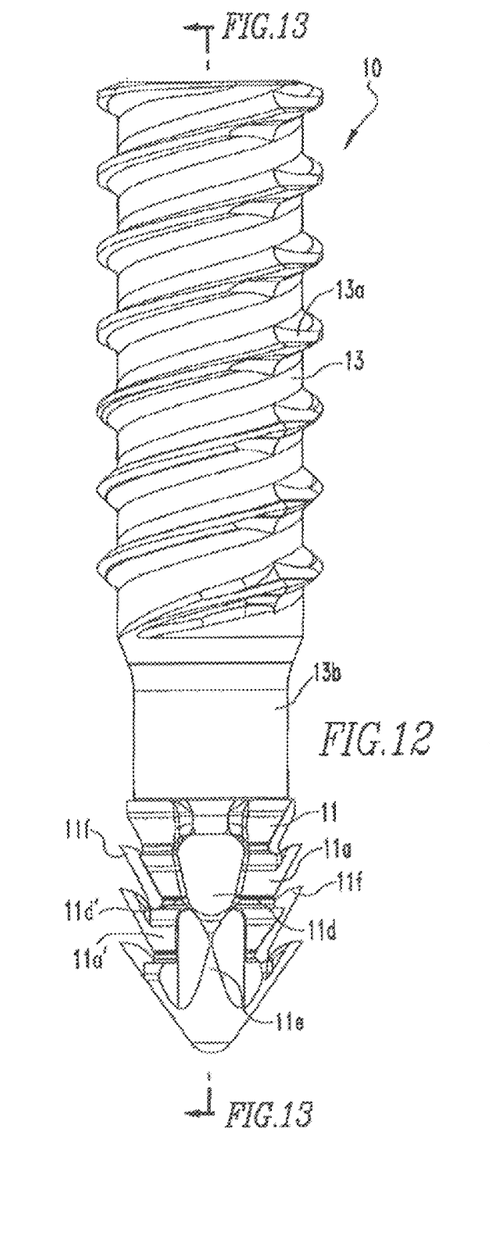
FIG. 12 shows a side view of the anchor assembly of the present disclosure after the anchor assembly is placed within bone.
Figure 13:
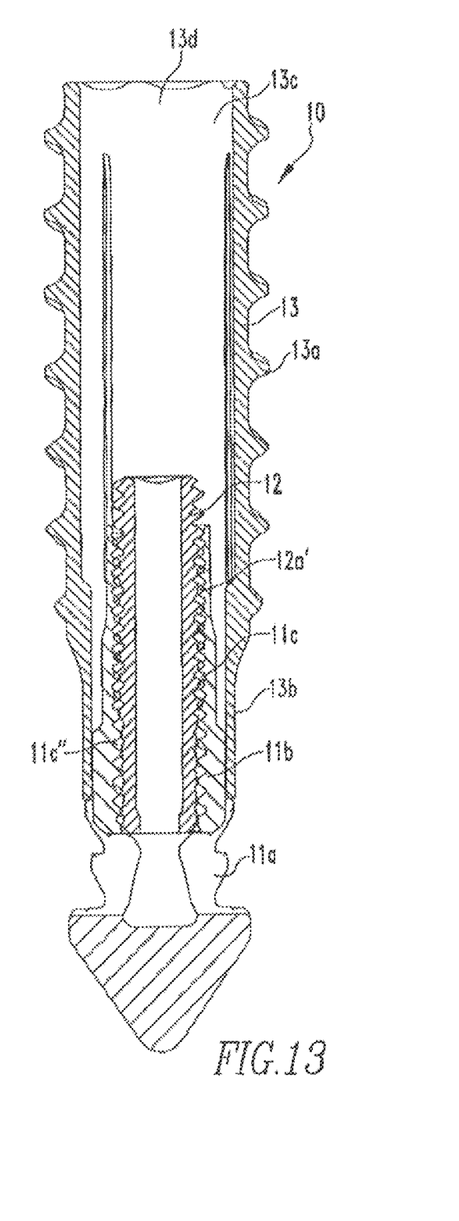
FIG. 13 shows a cross-sectional view of the anchor assembly of FIG. 12.

FIGS. 12 and 13 show the assembled anchor assembly 10 without the suture. The suture may be tensioned prior to advancing the insertion member 12 to engage the suture. Optionally, a suture anchor may be placed within bone, ends of the suture placed through the soft tissue, and the ends then placed through the through hole 11d of the anchor 11. Repair would continue as described above. A similar type of repair is shown and described in U.S. patent application Publication No. 2009/0112270, U.S. Pat. No. 8,974,494 issued Mar. 10, 2015 and U.S. Pat. No. 8,372,124 issued Feb. 12, 2013, the disclosures of which are incorporated herein by reference in their entireties.

The components of the anchor assembly are made from a polymer material and via an injection molding process. However, other materials and processes may be used. The handle and knobs of the delivery device are manufactured from a polymer material and via an injection molding process. The handle and knobs are coupled via an interference fit. However, other materials, processes of making and methods of coupling may be used. The components of the shaft are made from a metal material via an extrusion or drawings process. The components of the shaft are coupled to the handle and knobs via a threaded fit or an interference fit. However, other materials, processes of making and methods of coupling may be used.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

The invention claimed is:

1. An anchor delivery device, comprising:
    a handle;
    a first knob rotatably coupled to the handle;
    a second knob rotatably coupled to the handle; and
    a shaft coupled to the handle, the shaft including:
        an outer member having a proximal portion coupled to the first knob;
        an inner member disposed within the outer member; and
        a driver, disposed within the inner member, having a proximal portion coupled to the second knob,
    wherein each of the first and second knobs is configured to rotate without advancing along a longitudinal axis of the handle.

2. The anchor delivery device of claim 1, further comprising:
    a sleeve coupled to the outer member;
    an anchor coupled to the inner member; and
    an insertion member, disposed within the anchor, the insertion member coupled to the driver.

3. The anchor delivery device of claim 2, wherein the insertion member is inserted in a cavity of the anchor.

4. The anchor delivery device of claim 1, further comprising:
    a movable member coupling the first knob to the outer member proximal portion.

5. The delivery device of claim 4, wherein the movable member includes a distal portion, a proximal portion and a cannulation.

6. The delivery device of claim 5, wherein the movable member proximal portion includes threads on its outer surface.

7. The delivery device of claim 6, wherein the movable member is located in the handle cavity.

8. The delivery device of claim 7, wherein the handle cavity comprises:
    a handle cavity distal portion and a handle cavity proximal portion; and
    threads disposed on the handle cavity proximal portion configured to couple to the outer surface threads.

9. A suture anchor delivery device, comprising:
    a handle defining a cavity;
    a shaft, coupled to the handle, including:
        a shaft outer member;
        a shaft inner member disposed within the shaft outer member; and
    a first knob rotatably coupled to the handle;

a movable member coupled to the first knob and a proximal portion of the shaft outer member;

a second knob rotatably coupled to the handle; and a driver, disposed within the shaft inner member, coupled to the second knob, wherein each of the first and second knobs is configured to rotate without advancing along a longitudinal axis of the handle.

10. The delivery device of claim 9, wherein a proximal portion of the driver is coupled to the second knob.

11. The delivery device of claim 9, wherein the movable member includes a distal portion, a proximal portion and a cannulation.

12. The delivery device of claim 11, wherein the movable member proximal portion includes threads on its outer surface.

13. The delivery device of claim 12, wherein the movable member is located in the handle cavity.

14. The delivery device of claim 13, wherein the handle cavity comprises:

a handle cavity distal portion and a handle cavity proximal portion; and threads disposed on the handle cavity proximal portion configured to couple to the outer surface threads.

15. The delivery device of claim 9, further comprising:

a sleeve coupled to the shaft outer member;

an anchor coupled to the shaft inner member; and an insertion member, disposed within the anchor, the insertion member coupled to the driver.

16. The delivery device of claim 15, wherein the insertion member is inserted in a cavity of the anchor.

17. A suture anchor delivery device, comprising:

a handle;

a shaft, coupled to the handle;

a driver disposed within the shaft;

a movable member disposed in the handle;

a first knob, rotatably coupled to the handle, and rotatably coupled to the movable member, configured to advance the movable member distally within the handle when rotated with respect to the handle; and a second knob, rotatably coupled to the handle, and rotatably coupled to the driver, configured to advance the driver distally within the shaft when rotated with respect to the handle, wherein each of the first and second knobs is configured to rotate without advancing along a longitudinal axis of the handle.

18. The delivery device of claim 17, wherein the shaft includes a shaft outer member, the delivery device further comprising:

a sleeve coupled to the shaft outer member;

a shaft inner member disposed within the shaft outer member;

an anchor coupled to the shaft inner member; and an insertion member, disposed within the anchor, coupled to the driver.

19. The delivery device of claim 18, wherein the insertion member is inserted in a cavity of the anchor.

* * * * *